(12) United States Patent
Yoshikawa et al.

(10) Patent No.: US 8,422,019 B2
(45) Date of Patent: Apr. 16, 2013

(54) LIGHT MEASURING APPARATUS AND LIGHT MEASURING METHOD

(75) Inventors: Yumiko Yoshikawa, Minato-ku (JP); Tsutomu Ishi, Minato-ku (JP); Ryuji Funayama, Yokohama (JP); Shinya Kawamata, Gotenba (JP)

(73) Assignees: NEC Corporation, Tokyo (JP); Toyota Jidosha Kabushiki Kaisha, Aichi-ken (JP)

( * ) Notice: Subject to any disclaimer, the term of this patent is extended or adjusted under 35 U.S.C. 154(b) by 278 days.

(21) Appl. No.: 13/034,880

(22) Filed: Feb. 25, 2011

(65) Prior Publication Data

US 2011/0216323 A1 Sep. 8, 2011

(30) Foreign Application Priority Data

Mar. 5, 2010 (JP) ................................. 2010-049185

(51) Int. Cl.
*G01N 21/55* (2006.01)
(52) U.S. Cl.
USPC .......................................... 356/448; 356/445
(58) Field of Classification Search .......... 356/445–448, 356/450–458
See application file for complete search history.

(56) References Cited

U.S. PATENT DOCUMENTS

| | | | | |
|---|---|---|---|---|
| 3,089,383 A * | 5/1963 | Nearhoof et al. | ............. | 356/448 |
| 4,653,316 A * | 3/1987 | Fukuhara | ......................... | 73/146 |
| 4,690,553 A * | 9/1987 | Fukamizu et al. | ............... | 356/51 |
| 4,954,962 A * | 9/1990 | Evans et al. | ...................... | 701/28 |
| 5,747,813 A * | 5/1998 | Norton et al. | .................. | 250/372 |
| 5,962,853 A * | 10/1999 | Huth-Fehre et al. | ...... | 250/339.11 |
| 5,982,486 A * | 11/1999 | Wang | ............................. | 356/451 |
| 6,031,233 A * | 2/2000 | Levin et al. | ............... | 250/339.11 |
| 6,115,673 A * | 9/2000 | Malin et al. | ...................... | 702/23 |
| 6,240,372 B1 * | 5/2001 | Gross et al. | ...................... | 702/71 |
| 6,407,674 B1 * | 6/2002 | Gallagher | ...................... | 340/905 |
| 6,862,534 B2 * | 3/2005 | Sterling et al. | .................. | 702/23 |
| 6,922,583 B1 * | 7/2005 | Perelman et al. | ............. | 600/476 |
| 6,983,245 B1 | 1/2006 | Jimenez Felstrom et al. | ............................. | 704/238 |
| 7,298,869 B1 * | 11/2007 | Abernathy | ..................... | 382/108 |
| 7,471,385 B2 * | 12/2008 | Mestha et al. | ............. | 356/243.5 |
| 2007/0153277 A1 * | 7/2007 | Shakespeare et al. | ........ | 356/402 |

FOREIGN PATENT DOCUMENTS

DE 102007013830 A1 10/2008
JP 2001-066254 A 3/2001

OTHER PUBLICATIONS

Office Action dated Jul. 5, 2012 issued by the German Patent Office in counterpart German Application No. 10 2011 004 638.0.

* cited by examiner

*Primary Examiner* — Gregory J. Toatley
*Assistant Examiner* — Jarreas C Underwood
(74) *Attorney, Agent, or Firm* — Sughrue Mion, PLLC

(57) ABSTRACT

A light with a known spectrum is emitted from a light source toward a road surface, a first reflected light that is a reflected light of the known light reflected from the road surface is received by a first light receiver, and a reflectance spectrum of the light of the road surface is calculated from a spectrum of the first reflected light received by the first light receiver and the spectrum of the known light stored in the storage unit. A second reflected light that is reflected light of an environmental light reflected from the road surface is received by a second light receiver, and a spectrum of the environmental light is calculated from a spectrum of the second reflected light received by the second light receiver and the calculated reflectance spectrum of the light of the road surface.

8 Claims, 3 Drawing Sheets

LIGHT MEASURING APPARATUS AND LIGHT MEASURING METHOD

This application is based upon and claims the benefit of priority from Japanese patent application No. 2010-049185, filed on Mar. 5, 2010, the disclosure of which is incorporated herein in its entirety by reference.

TECHNICAL FIELD

The present invention relates to a light measuring apparatus and a light measuring method for measuring a spectrum of an environmental light.

BACKGROUND ART

For safer traveling of a vehicle, it is important to reduce blind spots of a driver, and also to quickly detect obstacles such as other automobiles, pedestrians, or bicycles around the vehicle, particularly, in front of the vehicle and to notify the driver of the obstacles in low visibility such as at night or in heavy weather. In recent years, various studies have been made for realizing a visibility assist apparatus that assists such visibility in driving.

With the visibility assist apparatus, if all objects around the vehicle are detected and notified to the driver, excessive information will given to the driver, which will interfere with attention to driving. Thus, a method for optically identifying an object has been studied so that only an object that is to be watched can be notified to a driver.

In order to optically identify an object, an emitted light or a light reflected from the object needs to be precisely extracted, and there is a need for a light measuring apparatus that obtains a spectrum of an environmental light applied to the object.

Although a method for obtaining a spectrum of an environmental light is not disclosed, for example, Japanese Patent Laid-Open No. 2001-66254A describes a method for removing background light such as an illumination light or an outside light in order to measure the strength or the like of a detected light (emitted light such as fluorescence).

Japanese Patent Laid-Open No. 2001-66254A describes a method for removing the background light by performing detection measurement for measuring a light including a detected light in the presence of two background lights Fa(t) and Fb(t) having different cycles, and by performing reference measurement for measuring light that does not include the detected light with time interval Tk set so as to be an integral multiple of a least common multiple of cycles fa and fb of the background lights, and subtracting measured value Sps obtained by the reference measurement from measured value Spc obtained by the detection measurement.

As described above, in order to optically identify an object, an emitted light or reflected light from the object needs to be extracted, and thus a spectrum of an environmental light applied to the object as a noise light needs to be obtained. At this time, if the spectrum of the environmental light cannot be stably obtained, a spectrum of the object cannot be stably obtained.

For example, in the case of an aircraft in the air where there are no objects, that block environmental light, around the aircraft, a light receiving sensor can be provided in an upper portion or the like of an airframe to directly measure a spectrum of the environmental light. However, for a vehicle traveling on a road, there are various artificial objects or natural objects therearound, and the spectrum of an environmental light momentarily changes. Thus, it is difficult to stably obtain a spectrum of environmental light by a direct measuring method.

SUMMARY

The present invention has an object to provide a light measuring apparatus and a light measuring method that can stably obtain a spectrum of environmental light.

In order to achieve the object, a light measuring apparatus according to an exemplary aspect of the present invention includes: a light source that emits a light with a known spectrum toward a road surface; a first light receiver that receives a first reflected light that is a reflected light of the known light reflected from the road surface; a second light receiver that receives a second reflected light that is a reflected light of an environmental light reflected from the road surface; a storage unit that previously stores data on the spectrum of the known light; and a calculator that calculates a reflectance spectrum of the light of the road surface from a spectrum of the first reflected light received by the first light receiver and the spectrum of the known light stored in the storage unit, and calculates a spectrum of the environmental light from a spectrum of the second reflected light received by the second light receiver and the calculated reflectance spectrum of the light of the road surface.

A light measuring method according to an exemplary aspect of the present invention includes: emitting a light with a known spectrum from a light source toward a road surface; receiving a first reflected light that is a reflected light of the known light reflected from the road surface with a first light receiver; calculating a reflectance spectrum of the road surface from a spectrum of the first reflected light received by the first light receiver and the spectrum of the known light previously stored in the storage unit; receiving a second reflected light that is a reflected light of an environmental light reflected from the road surface with a second light receiver; and calculating a spectrum of the environmental light from a spectrum of the second reflected light received by the second light receiver and the calculated reflectance spectrum of the light of the road surface.

EXEMPLARY EMBODIMENT

The present invention will now be described with reference to the drawings.

In a light measuring apparatus of the present invention, in a first stage, a light with a known spectrum is applied to a road surface to obtain a reflected light thereof. Data on the obtained spectrum and prepared data on the spectrum of the known light are used to calculate a reflectance spectrum of the light of the road surface. Then, in a second stage, a reflectance spectrum of the road surface to which an environmental light is applied is obtained, and data on the reflectance spectrum of the light of the road surface that is exposed to the environmental light and data on the reflectance spectrum of the light of the road surface previously calculated are used to calculate a spectrum of the environmental light. These processes in the two stages can be performed to stably obtain the spectrum of the environmental light that momentarily changes.

Figure 1:
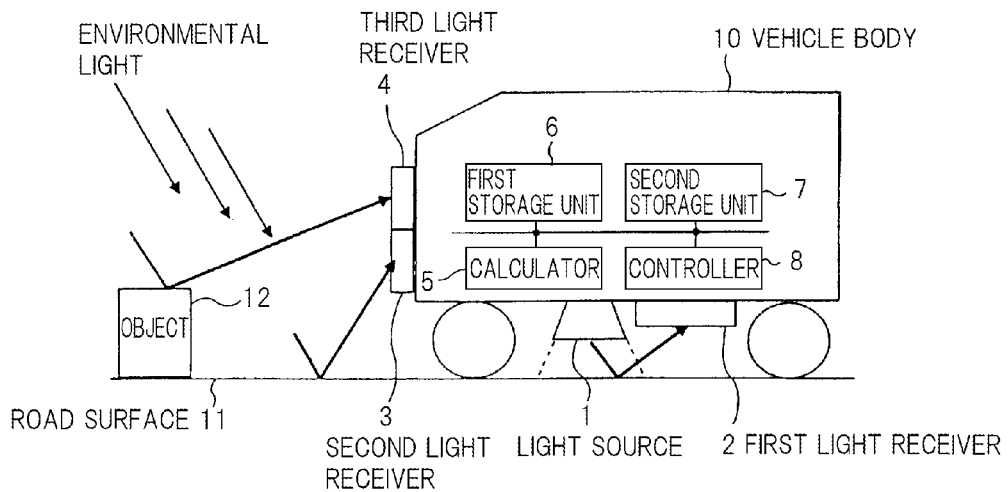
FIG. 1 is a block diagram showing an exemplary configuration of a light measuring apparatus of the present invention.

FIG. 1 is a block diagram showing an exemplary configuration of the light measuring apparatus of the present invention.

As shown in FIG. 1, the light measuring apparatus of the present invention includes light source 1, first light receiver 2, second light receiver 3, third light receiver 4, calculator 5, first storage unit 6, second storage unit 7, and controller 8, which are connected so that data can be transmitted and received.

Light source 1 is mounted to, for example, a lower portion of vehicle body 10, and emits a light with a known spectrum (hereinafter referred to as a known light) a toward road surface 11.

First light receiver 2 is a light receiving sensor that receives known light "a" (first reflected light) emitted from light source 1 and reflected from road surface 11. First light receiver 2 is mounted to, for example, the lower portion of vehicle body 10 that does not receive environmental light.

Second light receiver 3 is a light receiving sensor that receives reflected light (second reflected light) of the environmental light reflected from road surface 11. Second light receiver 3 is mounted to, for example, a side surface, a front surface, or a rear surface of vehicle body 10 so as to be able to receive the reflected light of the environmental light reflected from road surface 11.

Third light receiver 4 is a light receiving sensor that receives emitted light of object 12 to be detected or reflected light of the environmental light (third reflected light) reflected by object 12. Third light receiver 4 is mounted to, for example, the front surface of vehicle body 10 so as to be able to receive emitted light of object 12 or the reflected light of the environmental light reflected by object 12.

As second light receiver 3 and third light receiver 4, light receiving sensors having the same spectral sensitivity characteristic as first light receiver 2 are used. Second light receiver 3 and third light receiver 4 may have a spectral sensitivity characteristic different from that of first light receiver 2 as long as, for example, calculator 5 can correct an output value so as to have the same spectral sensitivity characteristic as first light receiver 2. Second light receiver 3 and third light receiver 4 may be realized using a common light receiving sensor as long as the reflected light from road surface 11 can be separated from the light from object 12. In this case, as means for separating the reflected light from road surface 11 from the light from object 12, for example, a mechanism for switching a light receiving surface of the light receiving sensor to road surface 11 or object 12, or a method for performing image processing of output data of the light receiving sensor with calculator 5 to differentiate road surface 11 from object 12 are conceivable.

First storage unit 6 is a memory that previously stores data on the spectrum of known light "a".

Calculator 5 uses data on the spectrum obtained using first light receiver 2, second light receiver 3, and third light receiver 4, and data on the spectrum of known light "a" stored in first storage unit 6 to calculate a reflectance spectrum of the light of the road surface, a spectrum of the environmental light, and a spectrum of object 12.

Second storage unit 7 is a memory that stores calculation results by calculator 5.

Controller 8 controls an operation of the entire light measuring apparatus including light source 1, first light receiver 2, second light receiver 3, third light receiver 4, calculator 5, first storage unit 6, and second storage unit 7.

Controller 8, calculator 5, first storage unit 6, and second storage unit 7 can be realized by a known information processing device (computer) including, for example, a CPU (Central Processing Unit), a DSP (Digital Signal Processor), a memory, an A/D (Analog to Digital) converter, a D/A (Digital to Analog) converter, and various logic circuits.

Next, operation of the light measuring apparatus of this embodiment will be described with reference to the drawings.

Figure 2:
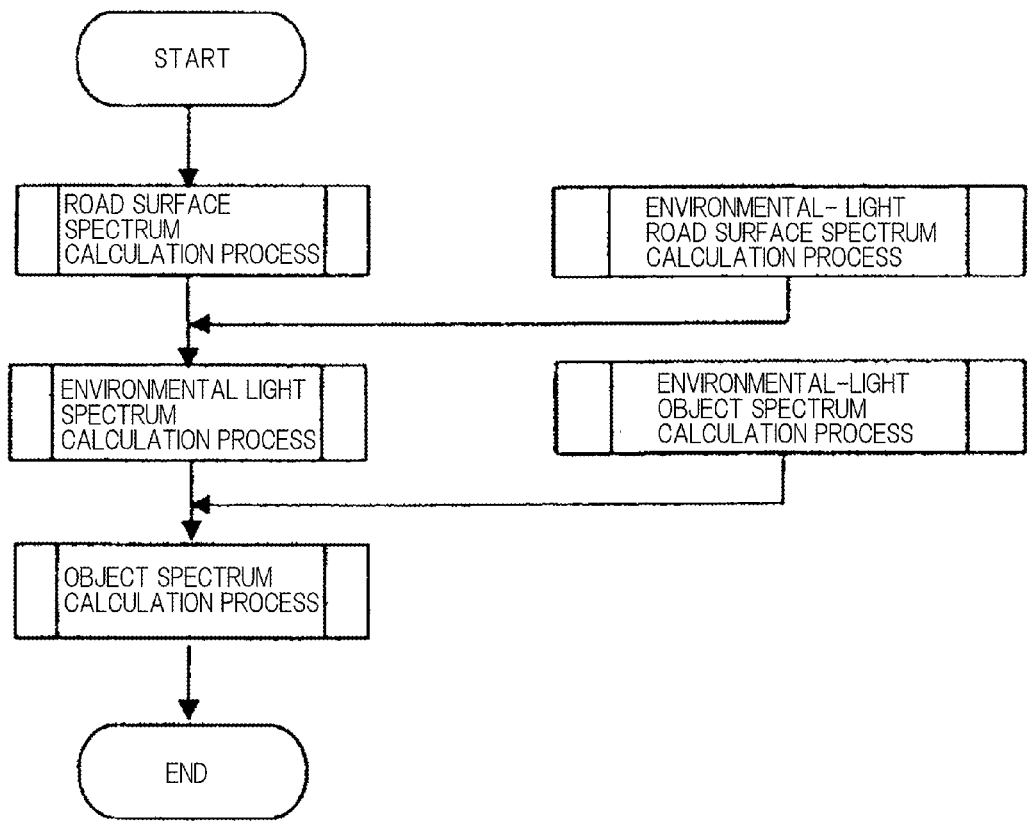
FIG. 2 is a flowchart showing a procedure of a process of the light measuring apparatus of the present invention.

FIG. 2 is a flowchart showing a procedure of a process of the light measuring apparatus of the present invention.

Figure 3:
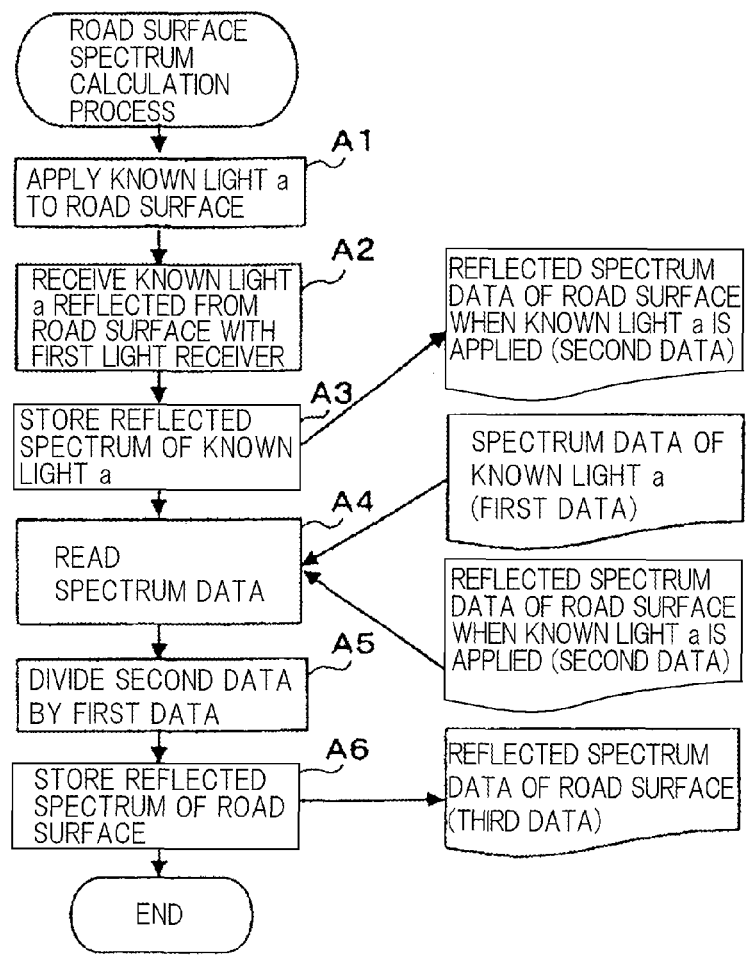
FIG. 3 is a flowchart of a procedure of a road surface spectrum calculation process shown in FIG. 2.
Figure 4:
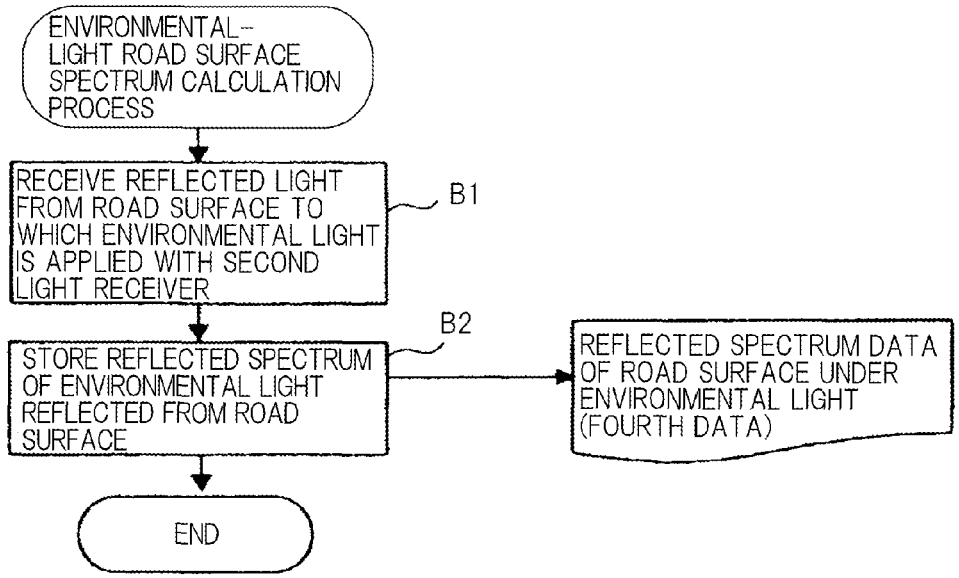
FIG. 4 is a flowchart of a procedure of an environmental-light road surface spectrum calculation process shown in FIG. 2.
Figure 5:
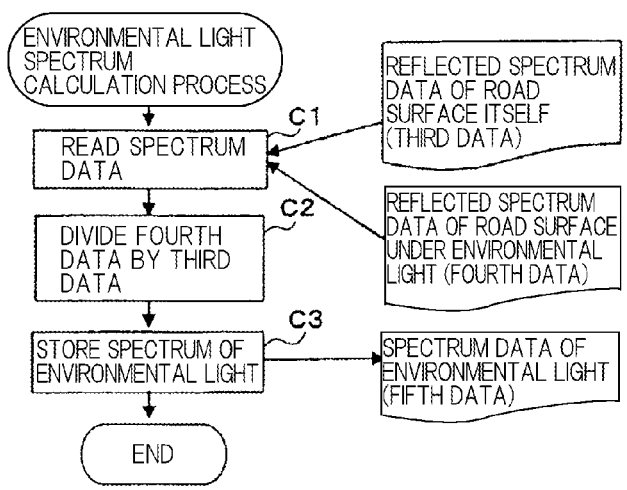
FIG. 5 is a flowchart of a procedure of an environmental light spectrum calculation process shown in FIG. 2.
Figure 6:
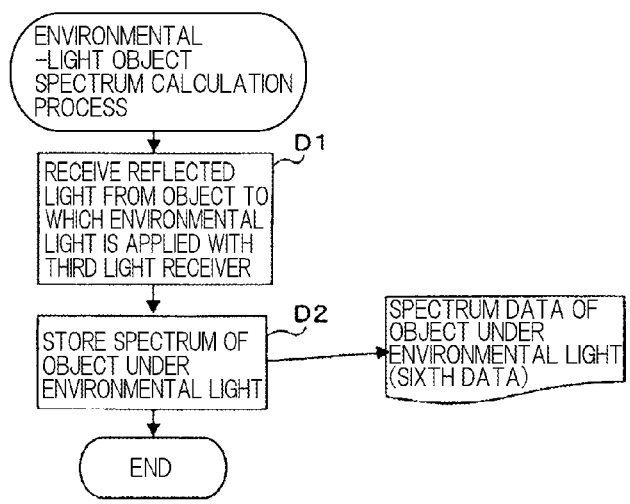
FIG. 6 is a flowchart of a procedure of an environmental-light object spectrum calculation process shown in FIG. 2.
Figure 7:
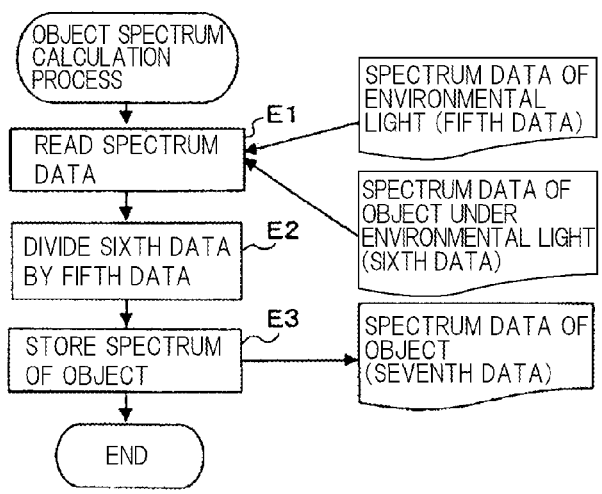
FIG. 7 is a flowchart of a procedure of an object spectrum calculation process shown in FIG. 2.

FIG. 3 is a flowchart of a procedure of a road surface spectrum calculation process shown in FIG. 2, and FIG. 4 is a flowchart of a procedure of an environmental-light road surface spectrum calculation process shown in FIG. 2. FIG. 5 is a flowchart of a procedure of an environmental light spectrum calculation process shown in FIG. 2, and FIG. 6 is a flowchart of a procedure of an environmental-light object spectrum calculation process shown in FIG. 2. FIG. 7 is a flowchart of a procedure of an object spectrum calculation process shown in FIG. 2. The processes of the light measuring apparatus of the present invention shown in FIGS. 2 to 7 are realized by the operations of light source 1, first light receiver 2, second light receiver 3, third light receiver 4, calculator 5, first storage unit 6, and second storage unit 7 according to instructions from controller 8.

As shown in FIG. 2, in the light measuring apparatus of the present invention, first in the spectrum road surface spectrum calculation process, known light "a" is used to calculate a spectrum of the reflected light of road surface 11. In the environmental-light road surface spectrum calculation process, a spectrum of the reflected light of road surface 11 that is exposed to the environmental light is obtained.

Then, in the light measuring apparatus of the present invention, in the environmental light spectrum calculation process, data on the spectrum of the reflected light of road surface 11 obtained in the road surface spectrum calculation process and data on the spectrum of the reflected light of road surface 11 that is exposed to the environmental light obtained in the environmental-light road surface spectrum calculation process are used to calculate a spectrum of the environmental light.

If the spectrum of the environmental light can be obtained, a spectrum of object 12 that is exposed to the environmental light is obtained in the environmental-light object spectrum calculation process, and in the object spectrum calculation process, data on the spectrum of the environmental light obtained in the environmental light spectrum calculation process and data on the spectrum of object 12 that is exposed to the environmental light obtained in the environmental-light object spectrum calculation process can be used to calculate the spectrum of object 12.

As shown in FIG. 3, in the road surface spectrum calculation process, controller 8 applies known light "a" to road surface 11 with light source 1 (Step A1), receives a reflected light of known light "a" reflected from road surface 11 with first light receiver 2, and obtains a spectrum of the reflected light of road surface 11 corresponding to known light "a" (Step A2). Then, data on the spectrum of the reflected light of road surface 11 corresponding to obtained known light "a" is stored as second data in second storage unit 7 (Step A3).

Then, controller 8 reads the data (first data) on the spectrum of known light "a" stored in first storage unit 6, reads the second data from second storage unit 7 (Step A4), and divides the second data by the first data with calculator 5 to calculate the spectrum of the reflected light of road surface 11 (Step A5). Then, the data on the spectrum of the reflected light of calculated road surface 11 is stored as third data in second storage unit 7 (Step A6).

As shown in FIG. 4, in the environmental-light road surface spectrum calculation process, controller 8 receives the reflected light from road surface 11 to which the environmental light is applied with second light receiver 3, and obtains a spectrum of the reflected light of road surface 11 that is exposed to the environmental light (Step B1). Then, data on the obtained spectrum of the reflected light of road surface 11 that is exposed to the environmental light is stored as fourth data in second storage unit 7 (Step B2).

As shown in FIG. 5, in the environmental light spectrum calculation process, controller 8 reads the third data and the fourth data from second storage unit 7 (Step C1), and divides the fourth data by the third data with calculator 5 to calculate a spectrum of the environmental light (Step C2). Then, data on the calculated spectrum of the environmental light is stored as fifth data in second storage unit 7 (Step C3).

As shown in FIG. 6, in the environmental-light object spectrum calculation process, controller 8 receives a reflected light from object 12 to which the environmental light is applied with third light receiver 4, and obtains a spectrum of the light of object 12 that is exposed to the environmental light (Step D1). Then, data on the obtained spectrum of the light of object 12 that is exposed to the environmental light is stored as sixth data in second storage unit 7 (Step D2).

As shown in FIG. 7, in the object spectrum calculation process, controller 8 reads the fifth data and the sixth data from second storage unit 7 (Step E1), and divides the sixth data by the fifth data with calculator 5 to calculate a spectrum of the light of object 12 (Step E2). Then, data on the calculated spectrum of object 12 is stored as seventh data in second storage unit 7 (Step E3).

According to the light measuring apparatus of this embodiment, known light "a" is emitted toward road surface 11, and first light receiver 2 mounted in a position that does not receive the environmental light receives the reflected light (known light "a") from road surface 11 to calculate the reflectance spectrum of the light of road surface 11 itself, thereby allowing the reflectance spectrum of road surface 11 to be stably obtained. The reflectance spectrum of the environmental light from road surface 11 received by second light receiver 3 and the calculated reflectance spectrum of the light of road surface 11 are used to calculate the spectrum of the environmental light. Thus, even if a vehicle or the like including the light measuring apparatus travels and the environmental light momentarily changes, the spectrum of the environmental light can be stably obtained. Thus, the calculated spectrum of the environmental light is used to calculate the spectrum of the light of object 12 to be detected, thereby allowing the spectrum of the light of object 12 to be stably obtained.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

The invention claimed is:

1. A light measuring apparatus comprising:
a light source that emits a light with a known spectrum toward a road surface;
a first light receiver that receives a first reflected light that is a reflected light of the known light reflected from said road surface;
a second light receiver that receives a second reflected light that is a reflected light of an environmental light reflected from said road surface;
a storage unit that previously stores data on the spectrum of said known light; and
a calculator that calculates a reflectance spectrum of the light of said road surface from a spectrum of said first reflected light received by said first light receiver and the spectrum of said known light stored in said storage unit, and calculates a spectrum of said environmental light from a spectrum of said second reflected light received by said second light receiver and the calculated reflectance spectrum of the light of said road surface.

2. The light measuring apparatus according to claim 1, wherein said calculator divides the spectrum of said first reflected light received by said first light receiver by the spectrum of said known light stored in said storage unit to calculate the reflectance spectrum of the light of said road surface, and
divides the spectrum of said second reflected light received by said second light receiver by the calculated reflectance spectrum of the light of said road surface to calculate the spectrum of said environmental light.

3. The light measuring apparatus according to claim 1, further comprising a third light receiver that receives a third reflected light that is a reflected light of the environmental light reflected from an object to be detected,
wherein said calculator calculates a reflectance spectrum of the light of said object from a spectrum of said third reflected light received by said third light receiver and the calculated spectrum of said environmental light.

4. The light measuring apparatus according to claim 1, wherein said second light receiver receives a third reflected light that is the reflected light of said environmental light reflected from said object to be detected so as to be separable from said second reflected light,
said calculator calculates the reflectance spectrum of the light of said object from the spectrum of said third reflected light received by said second light receiver and the calculated spectrum of said environmental light.

5. A light measuring method comprising:
emitting a light with a known spectrum from a light source toward a road surface;
receiving a first reflected light that is a reflected light of the known light reflected from said road surface with a first light receiver;
calculating a reflectance spectrum of said road surface from a spectrum of said first reflected light received by said first light receiver and the spectrum of said known light previously stored in a storage unit;
receiving a second reflected light that is a reflected light of an environmental light reflected from said road surface with a second light receiver; and
calculating a spectrum of said environmental light from a spectrum of said second reflected light received by said second light receiver and the calculated reflectance spectrum of the light of said road surface.

6. The light measuring method according to claim 5, further comprising:
- dividing the spectrum of said first reflected light received by said first light receiver by the spectrum of said known light stored in said storage unit to calculate the reflectance spectrum of the light of said road surface; and
- dividing the spectrum of said second reflected light received by said second light receiver by the calculated reflectance spectrum of the light of said road surface to calculate the spectrum of said environmental light.

7. The light measuring method according to claim 5, further comprising:
- receiving a third reflected light that is a reflected light of the environmental light reflected from an object to be detected with a third light receiver; and
- calculating a reflectance spectrum of the light of said object from a spectrum of said third reflected light received by said third light receiver and the calculated spectrum of said environmental light.

8. The light measuring method according to claim 5, further comprising:
- receiving a third reflected light that is the reflected light of the environmental light reflected from the light of said object to be detected so as to be separable from said second reflected light with said second light receiver; and
- calculating the reflectance spectrum of the light of said object from the spectrum of said third reflected light received by said second light receiver and the calculated spectrum of said environmental light.

\* \* \* \* \*